United States Patent
Paterson (10) Patent No.: US 6,565,852 B1
(45) Date of Patent: *May 20, 2003

(54) METHODS AND COMPOSITIONS FOR IMMUNOTHERAPY OF CANCER

(75) Inventor: Yvonne Paterson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/535,212

(22) Filed: Mar. 27, 2000

Related U.S. Application Data (63) Continuation-in-part of application No. 08/336,372, filed on Nov. 8, 1994, now Pat. No. 6,051,237.

(51) Int. Cl.[7] .................. A61K 39/02; A61K 39/145; A61K 39/00; A61K 38/00; C07H 21/02

(52) U.S. Cl. .................. 424/200.1; 424/234.1; 424/192.1; 424/277.1; 424/184.1; 424/185.1; 424/210.1; 536/23.1; 536/23.4; 536/23.72; 935/23; 935/27; 514/2

(58) Field of Search ............... 424/200.1, 234.1, 424/192.1, 277.1, 184.1, 185.1, 210.1; 514/2; 536/23.1, 23.4, 23.72; 935/27, 23

(56) References Cited

U.S. PATENT DOCUMENTS 5,830,702 A * 11/1998 Portnoy et al.
6,051,237 A *  4/2000 Paterson

FOREIGN PATENT DOCUMENTS

| WO | WO 99/06544 | * 2/1999 |
| WO | WO 99/10496 | * 3/1999 |

OTHER PUBLICATIONS

Zubair et al, In: Vaccines for human Papillomavirus Infection and Anogential Disease (ed. Robert W. Tindle); 1999, pp. 173–192.*
Ikonomidis et al, Vaccines 95, 1995, 95:317–326.*
Paterson et al, Proceedings of the American Association for Cancer Research, Mar. 2000, 41:890, abstract # S25.*
Pan et al, Cancer Research, Nov. 1, 1995, vol. 55:4776–4779.*
Stover et al., "New use of BCG for recombinant vaccines", Nature 1991, 351, 456–460.
Sun et al., "Isolation of Listeria monocytogenes Small–Plaque Mutants Defective for Intracellular Growth and Cell–to–Cell Spread", Infection and Immunity 1990, 58, 3770–3778.
Tilney, L.G. and D.A. Portnoy, Actin Filaments and the Growth, Movement, and Spread of the Intracellular Bacterial Parasite, Listeria monocytogenes, J. Cell Biol. 1989 109, 1597.
Townsend, S.E. and Allison, J.P., "Tumor Rejection After Direct Costimulation of CD8[+] T Cells by B7–Transfected Melanoma Cells", Science 1993, 259, 368–370.
Travis, J., "A Stimulating New Approach To Cancer Treatment", Science 1993 259, 310–311.
Weiskirch, L.M. and Paterson, Y., "Listeria monocytogenes: a potent vaccine vector for neoplastic and infectious disease", Immuno. Rev. 1997, 158, 159–169.
Wirth, R., F.Y. An and D. B. Clewell, "Highly Efficient Protoplast Transformation System for Streptococcus faecalis and a New Escherichia coli–S. faecalis Shuttle Vector", J. Bacteriol. 1986, 165, 831–836.
Zhang et al., "Selection of Tumor Antigens as Targets for Immune Attack Using Immunohistochemistry: Protein Antigens[1,2]", Clin. Cancer Res. 1998 4:2669.
Aggarwal et al., "Oral Salmonella: Malaria circumsporozoite Recombinants Induce Specific CD8+ Cytotoxic T Cells", J. of Exp. Med. 1990, 172, 1083–1090.
Boon et al., "Tumor Antigens Recognized by T Lymphocytes", Annu. Rev. Immunol. 1994, 12, 337–65.
Camilli et al., Dual roles of plcA in Listeria monocytogenes pathogenesis, Mol. Microbiol. 1993, 8, 143–157.
Cheever et al., "T–Cell Immunity to Oncogenic Proteins Including Mutated RAS and Chimeric BCR–ABL[a]", Annals N.Y. Acad. Sci. 1993 690:101–112.
Disis et al., "Immunity to the HER–2/neu oncogenic protein", Ciba Found. Symp. 1994 187:198–211.
Gansbacher et al., "Interleukin 2 Gene Transfer into Tumor Cells Abrogates Tumorigenicity and Induces Protective Immunity", J. Exp. Med. 1990, 172, 1217–1224.
Gillespie, A.M. and Coleman, R.E., "The potential of melanoma antigen expression in cancer therapy", Cancer Treat. Rev. 1999 25(4):219–27.
Golumbek et al., Treatment of Established Renal Cancer by Tumor Cells Engineered to Secrete Interleukin–4, Science 1991, 254, 713–716.
Finn, et al., MUC–1 Epithelial Tumor Mucin–Based Immunity and Cancer Vaccines, Immuno. Rev. 1995 145:61–89.
Kawashima et al., "The Multi–epitope Approach for Immunotherapy for Cancer: Identification of Several CTL Epitopes from Various Tumor–Associated Antigens Expressed on Solid Epithelial Tumors", Hum. Immunol. 1998 59:1–14.

(List continued on next page.)

Primary Examiner—Nita Minnifield
(74) Attorney, Agent, or Firm—Morgan, Lewis & Bockius, LLP (57) ABSTRACT

Methods and vaccines for inducing an immune response to a tumor associated antigen in a host are provided wherein the vaccine contains either a fusion protein of the tumor associated antigen fused to a truncated form of listeriolysin or a recombinant form of Listeria monocytogenes which grows and spreads and is capable of expressing the tumor associated antigen alone or as a listeriolysin fusion protein. Methods of suppressing formation of tumors and inhibiting growth of tumors in a host via administration of these vaccines are also provided.

2 Claims, 10 Drawing Sheets

OTHER PUBLICATIONS

McCarty et al., "Targeting p53 for Adoptive T–Cell Immunotherapy[1]", Cancer Research 1998 15:58 2601–5.

McKaig et al., "Human Papillomavirus and Head and Neck Cancer: Epidemiology and Molecular Biology", Head Neck 1998 20 (3):250–65.

Pagano, J.S., "Epstein–Barr Virus: The First Human Tumor Virus and its Role in Cancer", Proc. Assoc. Am. Physicians 1999 111(6) : 573–80.

Punwaney et al., "Human Papillomavirus May be Common within Nasopharyngeal Carcinoma of Caucasian Americans: investigation of Epstein–Barr virus and human papillomavirus in Eastern and Western Nasopharyngeal Carcinoma using Ligation–Dependent polymerase chain reaction", Head Neck 1999 21(1) :21–9.

Restifo et al., "Identification of Human Cancers Deficient in Antigen Processing", *J. of Exp. Med.*1993, 177, 265–272.

Schafer et al., "Induction of a Cellular Immune Response to a Foreign Antigen by a Recombinant *Listeria monocytogenes* Vaccine[1]", *J. Immunol.* 1992, 149, 53–59.

Serth et al., "Increased Levels of Human Papillomavirus Type 16 DNA in a Subset of Prostate Cancers[1]", Cancer Res. 1999 15:59(4):823–5.

* cited by examiner

METHODS AND COMPOSITIONS FOR IMMUNOTHERAPY OF CANCER

This application is a continuation-in-part of U.S. application Ser. No. 08/336,372, filed Nov. 8, 1994 now U.S. Pat. No. 6,051,237.

The invention was made in the course of work supported by the National Cancer Institute. The U.S. Government may have certain rights in this invention.

BACKGROUND OF THE INVENTION

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently being explored for cancer immunotherapy.

Elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., Annals N.Y. Acad. Sci. 1993 690:101–112). CD8+ T cells (TCD8+) in particular, which recognize Class I molecules of the major histocompatibility complex (MHC)-bearing peptides of 8 to 10 residues derived from proteins located in the cytosols, are believed to play an important role in this response. There are now numerous examples of both mouse and human TCD8+ that specifically recognize tumor cells and have therapeutic activity after adoptive transfer, in some cases inducing complete remission. However, despite the potential for T cells to eradicate tumors, it is obvious from the progressive growth of most cancers that many tumors escape recognition by TCD8+ in vivo. The induction of sufficient T cells in vivo has been difficult. Though a variety of tumors have been found to be immunogenic, stimulation of an effective anti-tumor immune response has been difficult to demonstrate.

One explanation for this phenomena is that tumors may be capable of delivering antigen-specific signals to T cells, but not the co-stimulatory signals necessary for full activation of T cells. Co-stimulation of T cells occurs when a surface molecule, B7, on the presenting cells interacts with a T cell molecule known as CD28. It has been observed that T cells receiving the antigen-specific signal (but not B7) become unresponsive. Many tumor cells do not carry the B7 protein, therefore B7 has been added to cancer cells (Travis, J., Science 1993 259, 310–311). It has been demonstrated that expression of the co-stimulatory ligand B7 on melanoma cells induced the rejection of a murine melanoma in vivo (Townsend, S. E. and Allison, J. P., Science 1993, 259, 368–370). This rejection was found to be mediated by CD8+ T cells; CD4+ T cells were not required. These results suggest that B7 expression may render tumor cells capable of effective antigen presentation, resulting in their eradication in vivo.

The effects of localized secretion of cytokines on tumor progression has also been studied. Secretion of low levels of interleukin-2 (IL-2) in a mouse fibrosarcoma cell line transfected with the human IL-2 gene introduced via a retroviral vector was found to abrogate the tumorigenicity of these cells and induce a long lasting protective immune response against a subsequent challenge with a tumorigenic dose of parent cells (Gansbacher et al., J. Exp. Med. 1990, 172, 1217–1224). In another study, cells from a spontaneously arising murine renal cell tumor were engineered to -secrete large doses of interleukin-4 (IL-4) locally (Golumbek et al., Science 1991, 254, 713–716). Animals injected with the tumor cells rejected the IL-4-transfected tumors in a predominantly T cell-independent manner. However, these animals developed a T cell-dependent systemic immunity to the parental tumor. The systemic immunity was tumor-specific and mediated by CDB+ T cells. These experiments suggest that it may be possible to cure parental tumors by generating a systemic immune response by the injection of genetically engineered tumor cells.

There is also evidence to suggest that some tumor cells express low levels of class I molecules in vivo and in vitro. Intracellular antigens must be processed before presentation to CD8+ T cells by major histocompatibility complex (MHC) class I molecules. The antigen processing efficiency of 26 different human tumor lines has been studied (Restifo et al., J. of Exp. Med. 1993, 177, 265–272). Three different cell lines, all human small cell lung carcinoma, consistently failed to process endogenously synthesized proteins for presentation to the T cells. Pulse chase experiments showed that MHC class I molecules were not transported by these cells lines from the endoplasmic reticulum to the cell surface. Northern blot analysis showed that these cells contained little or no mRNA encoding MHC-encoded proteosomes and transporter genes. Treatment with interferon γ enhanced expression of these mRNAs and reversed the observed functional and biochemical deficits. Thus, potential therapeutic applications which include enhancing antigen processing at the level of transcription of MHC-encoded proteosome and transporter genes was suggested.

Immunizing patients with recombinant BCG (bacille Calmette-Guèrin) or Salmonella bacteria carrying a gene coding for an antigenic peptide has also been suggested as an oral tumor immunotherapy (Boon et al. Annu. Rev. Immunol. 1994, 12, 337–65). Orally administered live attenuated Salmonella recombinant vaccine, which expressed the full length P. berghei circumsporozite antigen, has been shown to protect mice against malaria. This immune response was mediated by the induction of CD8+ T cells (Aggarwal et al., J. of Exp. Med. 1990, 172, 1083–1090). It is suggested that live attenuated Salmonella recombinants may be useful in the study of other diseases where CTL-mediated immunity may be important. However, no other experiments were reported. BCG has also been implicated as a novel live-vaccine vehicle which may prove useful in stimulating both humoral and cellular immune response to a wide variety of viral, bacterial and protozoal antigens (Stover et al., Nature 1991, 351, 456–460).

It has now been found that the immune response to an antigen, and in particular a tumor associated antigen, can be induced by the administration of a vaccine comprising a listeriolysin fusion protein comprising a tumor associated antigen or a recombinant form of the intracellular bacterium Listeria monocytogenes which expresses a tumor associated antigen or fragment thereof. The recombinant form of Listeria monocytogenes can express the tumor associated antigen alone or as a listeriolysin fusion protein which comprises the tumor associated antigen. In one embodiment, one or more vectors comprising recombinant Listeria monocytogenes each expressing a different tumor associated antigen or fusion protein thereof, can be used in a vaccine to stimulate an immune response. In this embodiment, it is preferred that the expressed tumor associated antigens be fused to listeriolysin. In another embodiment, one or more fusion proteins, each fusion protein comprising a truncated form of listeriolysin fused to a different tumor associated antigen, can be used. As demonstrated herein, administration of the vaccines of the present invention decrease the size of existing tumors and inhibit formation of primary tumors. No other stimulation following antigen presentation was required to induce this response.

SUMMARY OF THE INVENTION

An object of the present invention is to provide a method of inducing an immune response to a tumor associated antigen in a host which comprises administering to a host having cancer an effective amount of a vaccine comprising a fusion protein of the tumor associated antigen fused to a truncated form of listeriolysin, or a recombinant form of *Listeria monocytogenes* which grows and spreads and is capable of expressing a tumor associated antigen. In this method, the recombinant form of *Listeria monocytogenes* can express the tumor associated antigen alone or as a listeriolysin fusion protein which comprises the tumor associated antigen.

Another object of the present invention is to provide fusion proteins which comprise tumor associated antigens fused to a truncated form of listeriolysin.

Another object of the present invention is to provide a vaccine for inducing an immune response to a tumor associated antigen which comprises a fusion protein of a tumor associated antigen fused to a truncated form of listeriolysin, or a recombinant form of *Listeria monocytogenes* which grows and spreads and is capable of expressing a tumor associated antigen. The recombinant form of *Listeria monocytogenes* used in these vaccines can express the tumor associated antigen alone or as a listeriolysin fusion protein which comprises the tumor associated antigen.

Another object of the present invention is to provide a method of suppressing formation of tumors in a host comprising administering to a host an effective amount of a vaccine comprising a fusion protein of a tumor associated antigen fused to a truncated form of listeriolysin, or a recombinant form of *Listeria monocytogenes* which grows and spreads and is capable of expressing a tumor associated antigen. In this method, the recombinant form of *Listeria monocytogenes* can express the tumor associated antigen alone or as a listeriolysin fusion protein which comprises the tumor associated antigen.

Yet another object of the present invention is to provide a method of inhibiting growth and/or killing tumor cells in a host comprising administering to a host an effective amount of this vaccine.

BRIEF DESCRIPTION OF THE DRAWINGS

FIGS. 1 through 4 provide line graphs from experiments wherein mice were immunized with either saline (●), *L. monocytogenes* (■), or recombinant *L. monocytogenes* transformed to express influenza nucleoprotein (LM-NP) (♦) and then subsequently challenged with either CT26 or RENCA which had been transfected with the same influenza nucleoprotein (NP) gene that was used to transform the *L. monocytogenes* vector (CT26-NP or RENCA-NP, respectively) or with the parental CT26 or RENCA line.

FIG. 5 is a bar graph which provides data from experiments wherein it was shown that CTL generated by immunizing Balb/c mice with LM-NP can kill tumor cells CT26 and RENCA that express NP in vitro.

DETAILED DESCRIPTION OF THE INVENTION

The immune response to *L. monocytogenes* has been shown to be a TH1, CD4+ T cell and CD8+ T cell response with only very weak humoral responses being engendered. Recombinant forms of the wild-type bacterium have been developed which express the foreign proteins β-galactosidase (Schafer et al., *J. Immunol.* 1992, 149, 53–59), influenza nucleoprotein and HIV gag and nef gene product. Recombinant techniques have been developed to stably integrate these proteins into the Listerial chromosome in such a way that they are secreted by the bacterium. All of these recombinant vectors elicit strong, antigen specific, CTL responses in vivo. Thus, this bacterium serves as an ideal vector for boosting the CTC response to antigens, and in particular tumor associated antigens, and provides a unique system to prime the cellular immune response as a vaccine against various diseases, and in particular cancer.

Administration of a live vector such as *L. monocytogenes* results in a long lasting cellular immunity which often cannot be induced with killed preparations or soluble protein and adjuvant. A unique feature of the life-cycle of *L. monocytogenes* is that it invades the host cell and is taken up into a phagosome from which it escapes and then lives and replicates in the cytoplasm. Tilney, L. G. and D. A. Portnoy, *J. Cell Biol.* 1989 109, 1597. Thus, the *L. monocytogenes* vector provides the ability to target foreign proteins and fragments of proteins to the class I MHC restricted pathway. In addition to being a more efficacious vector, *L. monocytogenes*, which is a gram-positive organism, is also much safer than many other live vectors since it is very susceptible to most antibiotics, including penicillin. It also does not have the problems associated with toxicity from endotoxin which gram negative vectors such as Salmonella sp. present. Pre-existing immunity which could prevent effective boosting by a vector which has already been widely used as a vaccine, e.g., Vaccinia or BCG, is not likely to be a problem for *L. monocytogenes*, which has not been used previously in vaccine development. Mutant strains of *L.*

*monocytogenes*, which are avirulent but still induce good immunity, are also available for testing as potential vaccine candidates.

Using a model murine system, it has now been found that *L. monocytogenes* can induce an immune response against a protein expressed by tumor cells. This immune response causes the rejection of tumor cells that have been transferred to healthy, immunized mice and kills tumor cells in mice in which tumor cell growth has already been initiated. See FIGS. 3 through 7.

The ability of a vaccine comprising recombinant *L. monocytogenes* to convey specific protective immunity against the growth of CT26, a mouse colorectal carcinoma tumor and RENCA, a murine renal carcinoma, was examined. In preliminary experiments, *L. monocytogenes* was engineered to secrete nucleoprotein (NP) from A/PR/8/34 as a fusion protein with a major secreted Listerial protein, listeriolysin O (LLO), the product of the hemolysin gene. LLO is normally expressed and secreted in a host vacuole by *L. monocytogenes* and is required for escape of the bacteria into the cytoplasm. The ability of NP secreting *L. monocytogenes* recombinants to target the class I pathway of antigen processing for recognition by bulk influenza specific T cells from three strains of mice was tested. It was determined that the LLO-NP fusion proteins are appropriately processed for presentation by the three MHC class I haplotypes to which the A/PR/8/34 response is restricted, i.e., $K^d$, $D^b$ and $K^k$. Immunization of Balb/c mice with varying doses of LM-NP was demonstrated to result in a strong anti-NP CTC response.

Figure 1:
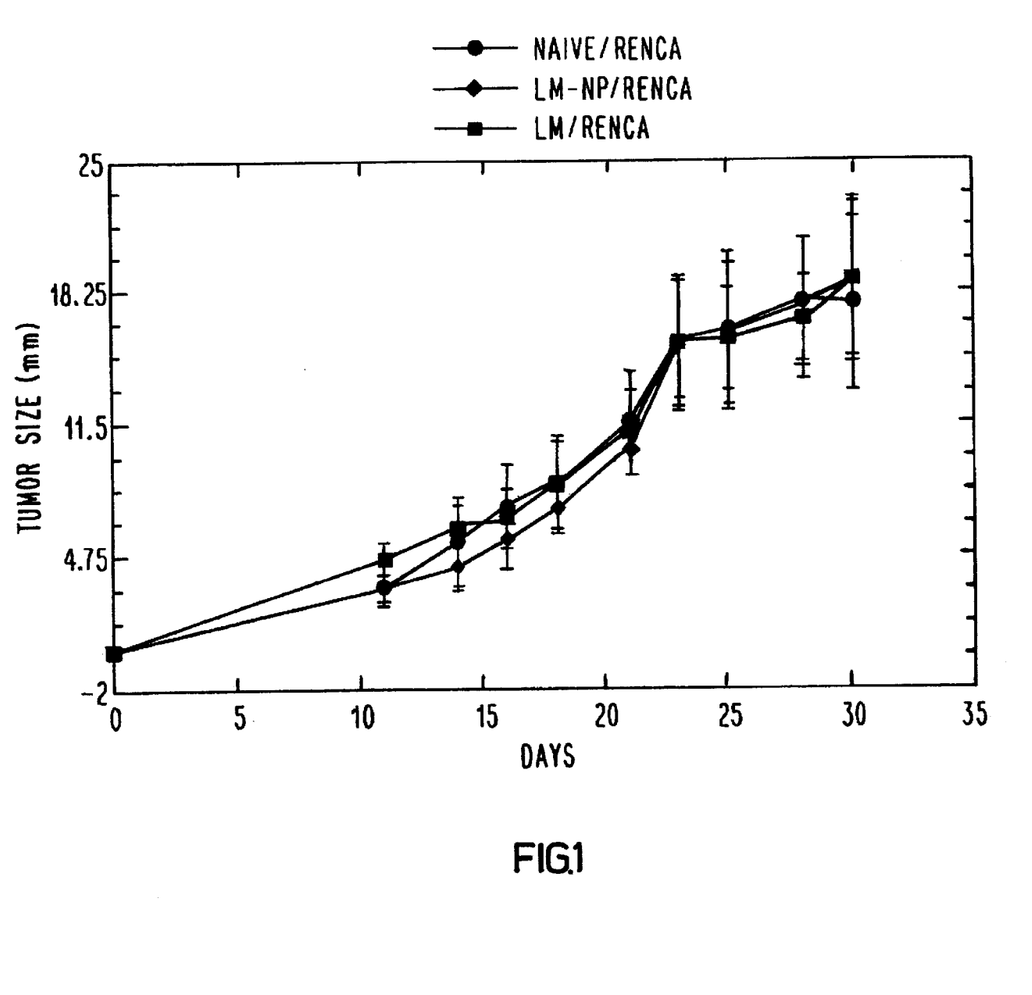
FIG. 1 provides data from experiments wherein mice in each immunization group were challenged with parental RENCA.
Figure 2:
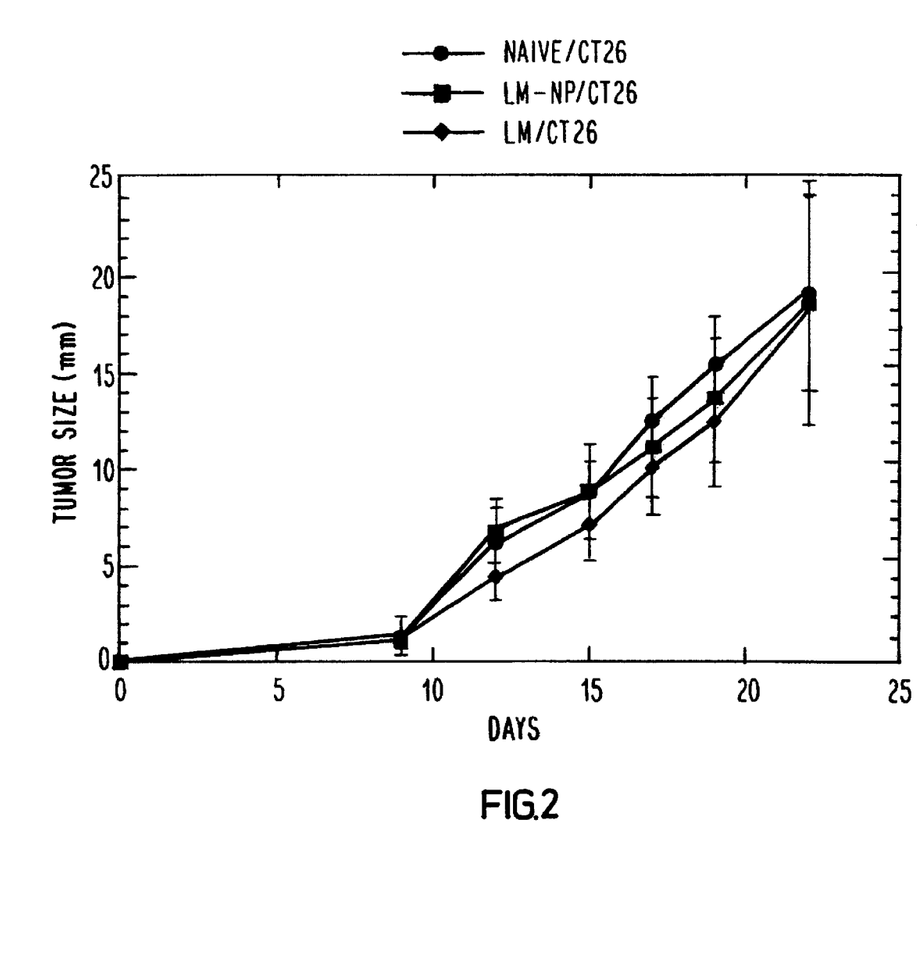
FIG. 2 provides data from experiments wherein mice in each immunization group were challenged with parental CT26.
Figure 3:
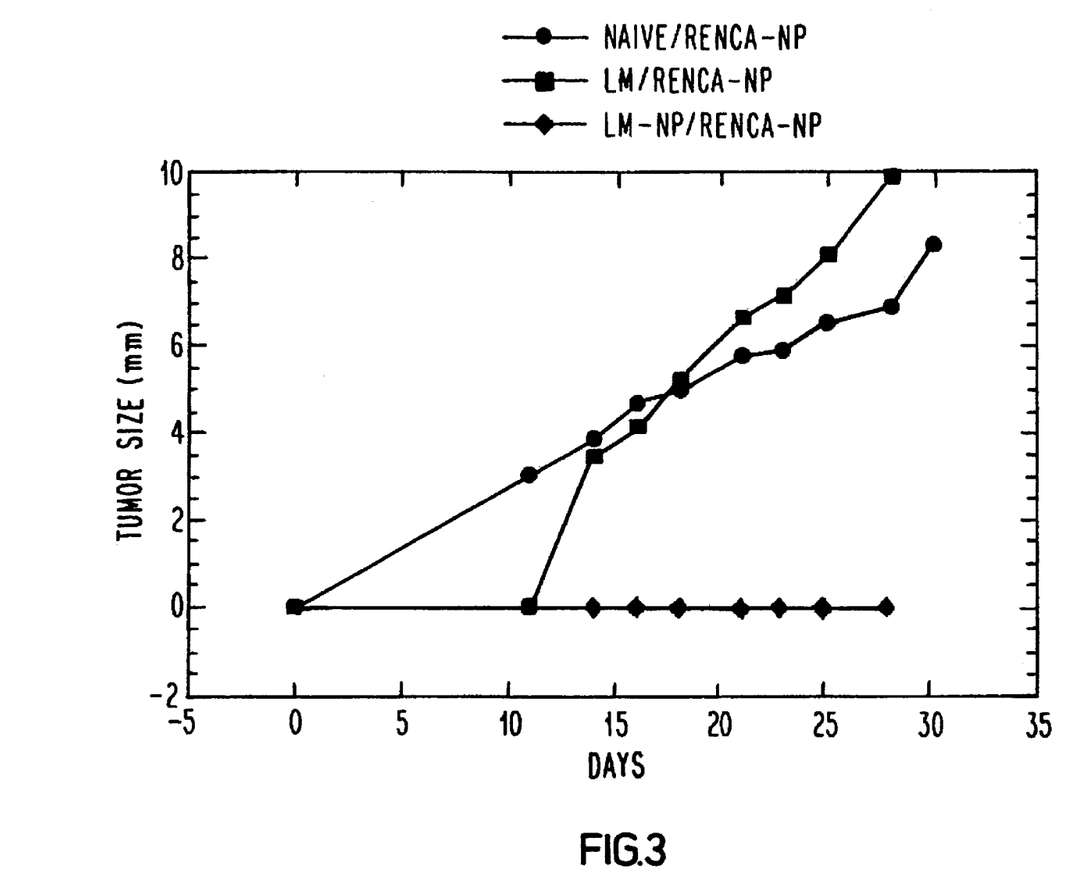
FIG. 3 provides data from experiments wherein mice from each immunization group were challenged with RENCA transfected with the same NP used to transform the *L. monocytogenes* (RENCANP).
Figure 4:
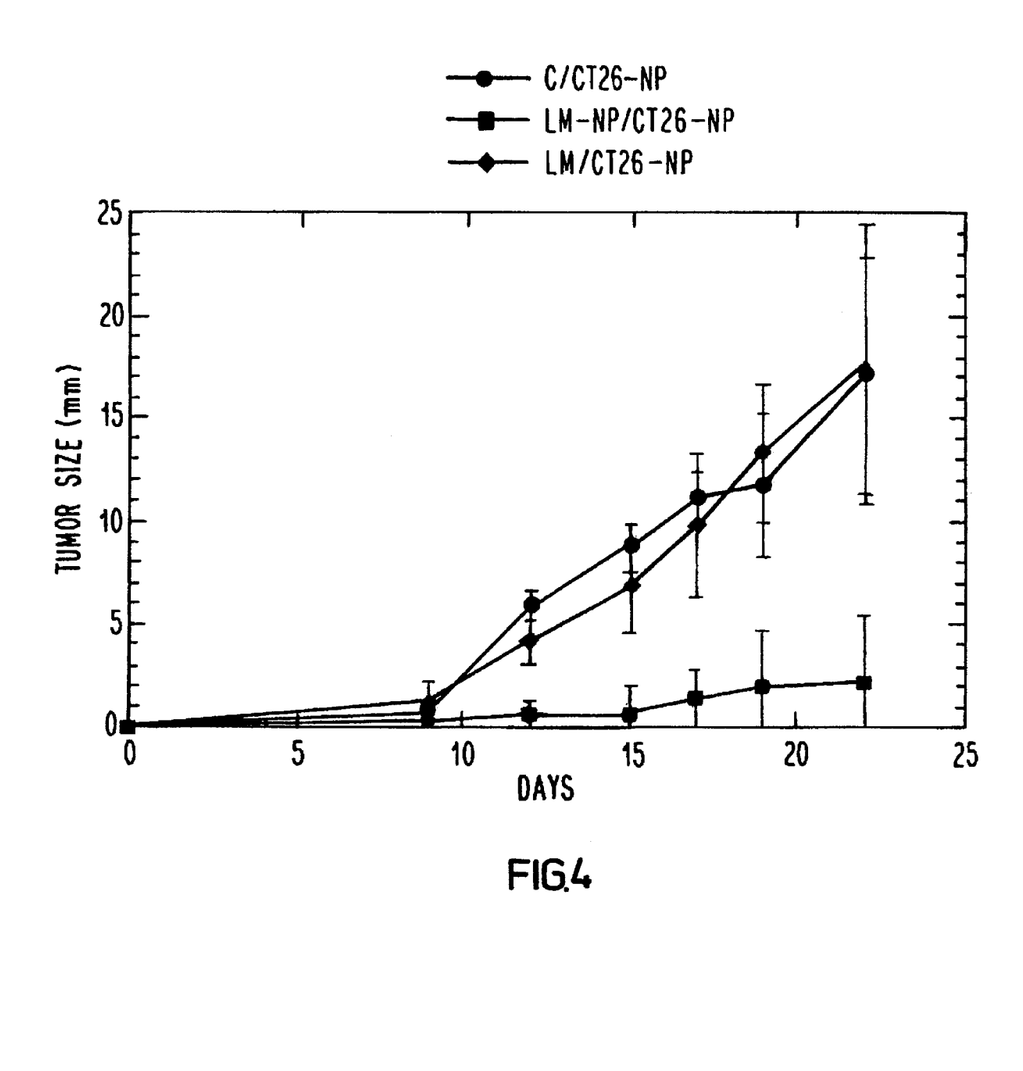
FIG. 4 provides data from experiments wherein mice from each immunization group were challenged with CT26 transfected with the same NP used to transform the *L. monocytogenes* (CT26NP).

In further experiments, mice were divided into three groups. One group was immunized with one-tenth of an $LD_{50}$ of wild-type *L. monocytogenes*, one group was immunized with sterile saline, and the third group was immunized with a vaccine comprising a recombinant *L. monocytogenes* vector which was transformed to secrete a fusion protein comprising influenza nucleoprotein (LM-NP) and a truncated form of listeriolysin. In this fusion protein, the listeriolysin is truncated to eliminate the hemolytic activity of the enzyme. After two weeks, each group received a similar booster immunization. This immunization schedule was determined to produce strong CTL responses against influenza nucleoprotein. Two weeks after the last immunization, animals in each group were challenged subcutaneously with a tumoricidal dose of either CT26 or RENCA which had been transfected with the same influenza nucleoprotein gene that was used to transform the *L. monocytogenes* vector (CT26-NP or RENCA-NP, respectively) or with the parental CT26 or RENCA line. Tumor growth was monitored. As shown in FIGS. 3 and 4, animals which received recombinant *Listeria monocytogenes* expressing NP-fusion protein (LM-NP) and which were challenged with the relevant tumor cell expressing NP were protected from further tumor formation. In the CT26-NP group, after 25 days, 6 of the animals showed no detectable tumor growth, 3 had tumors of less than 5.0 mm and one had a tumor of 9.0 mm (see FIG. 4). In the RENCA-NP group, none of the animals showed any signs of tumor growth (see FIG. 3). In contrast, all the mice in the other groups developed tumors between 1.5 and 3.0 cm (see FIGS. 1 and 2).

Figure 6:
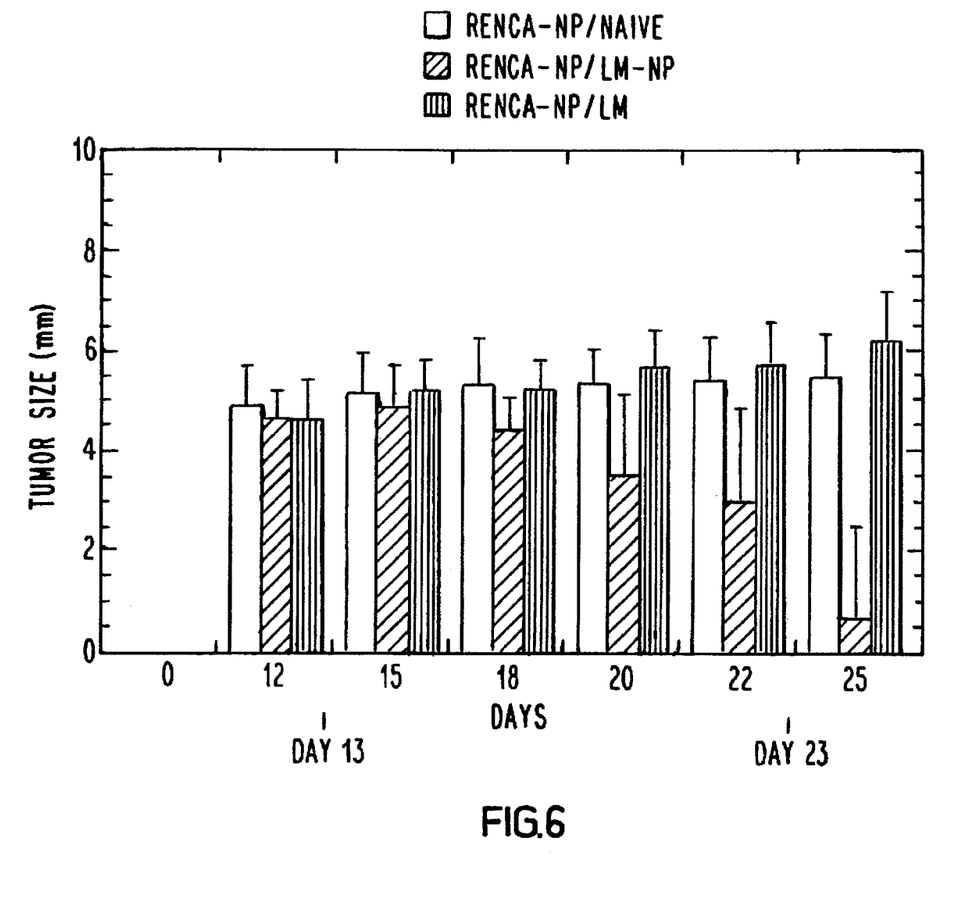
FIG. 6 is a bar graph which provides data from experiments wherein it was shown that immunization by LM-NP causes elimination of RENCA-NP tumor growth.
Figure 7:
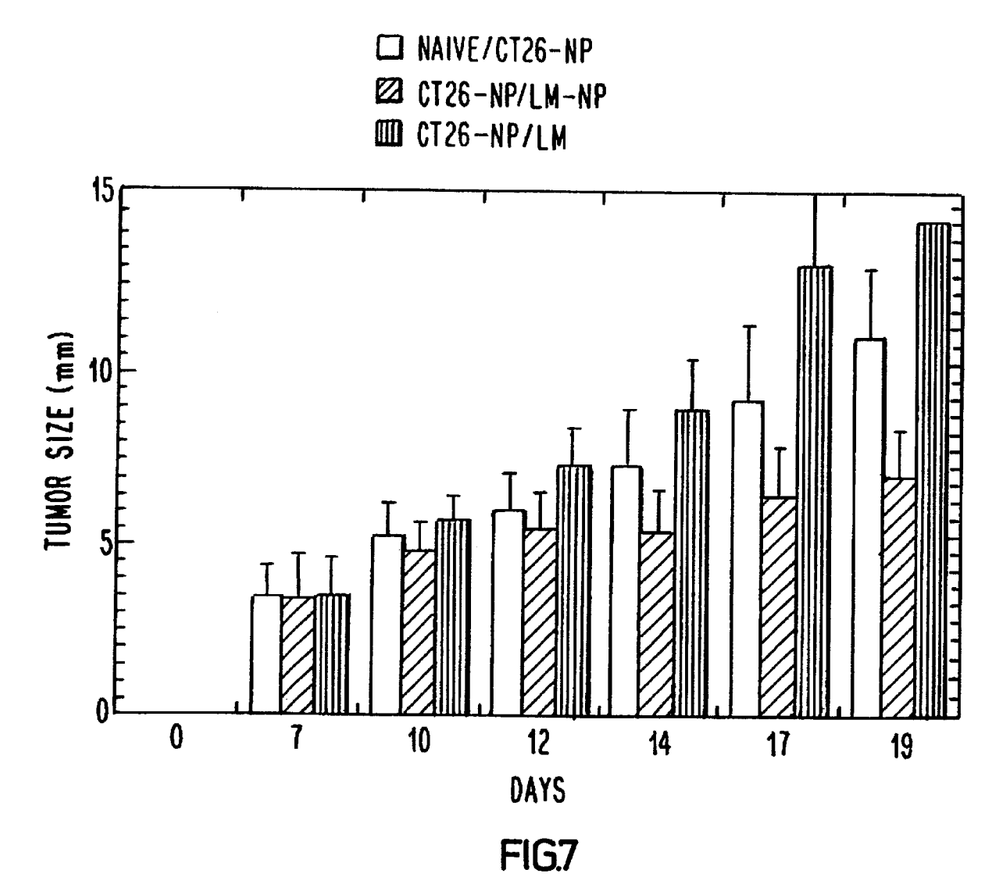
FIG. 7 is a bar graph which provides data from experiments wherein it was shown that immunization by LM-NP causes cessation of CT26-NP tumor growth.

The ability of LM-NP fusion protein to cause regression and depletion of existing tumors was also demonstrated. Tumor cells (either CT26 or RENCA cells) were introduced subcutaneously into mice. After the formation of measurable tumors, the mice were divided into three separate groups. A first group of mice received LM-NP, a second group of mice received wild type *Listeria monocytogenes* and a third group of mice received no further treatment. Mice in groups 1 and 2 were given a subsequent booster of either LM-NP or wild type *Listeria monocytogenes*, respectively. As shown in FIGS. 6 and 7 only the mice that received the vaccine with the LM-NP fusion protein showed regression of tumor growth to the point where the tumor was no longer visible.

Various tumor associated antigens have been identified. Further, much research effort is being expended to identify additional tumor associated antigens. Some groups of tumor associated antigens, also referred to in the art as tumor specific antigens, are tissue specific. Examples include, but are not limited to, tyrosinase for melanoma, PSA and PSMA for prostate cancer and chromosomal cross-overs such as bcr/abl in lymphoma. However, many tumor associated antigens identified occur in multiple tumor types, and some, such as oncogenic proteins which actually cause the transformation event, occur in nearly all tumor types. For example, normal cellular proteins that control cell growth and differentiation, such as p53 and HER-2/neu, can accumulate mutations resulting in upregulation of expression of these gene products thereby making them oncogenic (McCartey et al. Cancer Research 1998 15:58 2601–5; Disis et al. Ciba Found. Symp. 1994 187:198–211). These mutant proteins can be the target of a tumor specific immune response in multiple types of cancer. Transforming proteins from oncogenic viruses such as E6 and E7 from HPV or EBNA1 from Epstein Barr virus (EBV) also occur in many tumor types and can be the target of a tumor specific immune response in multiple types of cancer (McKaig et al. Head Neck 1998 20(3):250–65; Punwaney et al. Head Neck 1999 21(1):21–9; Serth et al. Cancer Res. 1999 15:59(4):823–5; Pagano, J. S. Proc. Assoc. Am. Physicians 1999 111(6):573–80). Non-oncogenic host proteins such as MAGE and MUC family are also ubiquitous. Specifically, the MAGE family of antigens have been found in many different cancers including breast cancer, lung cancer, esophageal cancer, hepatic cancer, thyroid cancer, neuroblastoma, gastric cancer, multiple myeloma and melanoma (Gillespie, A. M. and Coleman, R. E. Cancer Treat. Rev. 1999 25(4):219–27). The MUC family of antigens has been associated with ovarian and endometrial cancer, breast cancer, multiple myeloma, pancreatic cancer, and colon and rectal cancer (Segal-Eiras, A. and Croce, M. V. Allergol. Immunopathol. 1997 25(4):176–81). As will be obvious to those of skill in the art upon this disclosure, the invention is also applicable to other tumor associated antigens not specifically listed herein.

Further, as demonstrated by these reports, most cancers are associated with more than one antigen. Examples of tumors that express more than one tumor antigen include, but are not limited to, breast cancer which has been shown to be associated with MUC-1, HER-2/neu, MAGE, p53, T/Tn and CEA, colon cancer which has been shown to be associated with MUC-2 and MUC-4, CEA, p53 and the MAGE family, melanoma which has been shown to be associated with members of the MAGE family, MART-1 and gp100, and prostate cancer which has been associated with GM2, Tn, sTn, Thompson-Friedenreich antigen (TF), MUC1, MUC2, the beta chain of human chorionic gonadotropin (hCG beta), HER2/neu, PSMA and PSA. In fact, panels of antigens have been suggested for use in immunotherapy against cancer to compensate for the fact that antigen-loss variants of the tumors can grow out under immune system pressure (Zhang et al. Clin. Cancer Res. 1998 4:2669; Kawashima et al. Hum. Immunol. 1998 59:1). Accordingly, in a preferred embodiment of the present invention, the vaccine comprises a cocktail of recombinant L. monocytogenes, each expressing a different tumor associated antigen or a cocktail of fusion proteins, each fusion protein comprising a different tumor associated antigen fused to a truncated form of listeriolysin.

Very stable transformants which secrete a number of large viral proteins have been produced routinely using techniques routine to those of skill in the art. Several techniques for producing recombinant L. monocytogenes are known.

For example, integration in the Listerial chromosome as a result of a transposon insertion is described by Sun et al. (*Infection and Immunity* 1990, 58, 3770–3778) in the construction of DP-L967. Transposon mutagenesis has the advantage that a stable genomic insertion mutant can be formed but the disadvantage that the position in the genome where the foreign gene has been inserted is unknown. A L. monocytogenes recombinant that expresses E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The resulting recombinant is referred to herein as Lm-AZ/E7.

Figure 9:
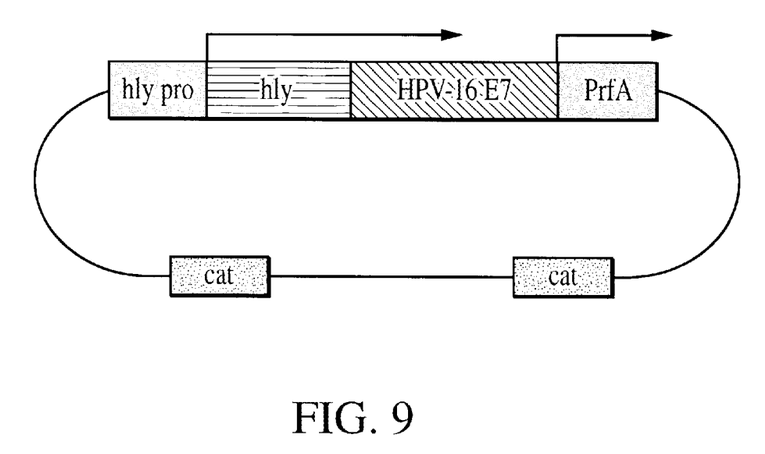
FIG. 9 is a diagram of a preferred multi-copy plasmid containing prfA and E7 fused to hly.

Cloning of the gene into a prfA-containing vector and using this plasmid to complement a prfA(−) Listeria mutant has been used to construct DP-L2028. DP-L2028 is the influenza NP expressing strain used in the tumor protection experiments. A L. monocytogenes vector that expresses an E7 fusion protein has also been constructed via this technique. Lm-GG/E7 was made by complementing a prfA-deletion mutant with a plasmid (see FIG. 9) containing a copy of the prfA gene and a copy of the E7 gene fused to a form of the LLO (hly) gene truncated to eliminate the hemolytic activity of the enzyme. Functional LLO is maintained by the organism via the endogenous chromosomal copy of hly. Accordingly, the form and level of expression of E7 by the GG construct is identical to Lm-NP.

Several approaches may be taken to express the tumor antigen in Listeria sp. as will be understood by one skilled in the art based upon this disclosure. One example is to generate a fusion protein of the selected tumor antigen and a Listerial protein such as Listeriolysin O or PI-PLC. Another way is through the use of a signal sequence, for a secreted Listerial protein such as hemolysin or phospholipases, employed downstream of a Listerial promoter. The promoters of various L. monocytogenes genes may be used to express foreign antigens. In addition, these genes may be used to generate fusion proteins with foreign antigens. For example, promoters for the genes hly, actA, plcA, plcB and mpl, which encode the Listerial proteins hemolysin, actA (a surface protein necessary for host cell actin assembly and essential for cell to cell spread of the bacterium), phosphotidylinositol-specific phospholipase, phospholipase C, and metalloprotease, respectively, can be used.

Another preferred method for producing these recombinants is integration into the Listeria chromosome by homologous recombination with a temperature sensitive plasmid. This method can be used to produce stable transformants that secrete the protein of interest. Unlike the case with transposon mutagenesis, the site of insertion is known. This method allows for the routine insertion of any gene of interest into the chromosome of L. monocytogenes which is then expressed under the control of a L. monocytogenes promoter. One such promoter, the hemolysin promoter, regulates the expression of hly, the Listerial gene which encodes LLO, an abundantly synthesized and secreted protein. Inclusion of the LLO signal sequence allows for the secretion of the expressed protein outside the bacterial cell wall. The construction of these stable recombinants of L. monocytogenes utilize regions of its chromosome that can act as sites for insertion without disrupting bacterial genes necessary for the growth and spread of the organism (Camilli et al., *Mol. Microbiol.* 1993, 8, 143–157; Weiskirch, L. M. and Paterson, Y. Immunol. Rev. 1997, 158, 159–169). These homology regions are introduced into the shuttle vector pKSV7, a temperature sensitive plasmid that functions in both *E. coli* and *L. monocytogenes*. An EcoR1 site near its center is then used to insert a series of DNA fragments between the two halves of these regions. After the addition of a polylinker, the promoter sequence of the Listeria hemolysin gene is inserted. Along with the promoter, downstream sequence information for the first 26 amino acids of the LLO protein (the signal sequence) and four additional amino acids is included to ensure proper processing of the signal sequence. The transcription termination sequence of the hemolysin gene is also included to ensure that stable and regulated synthesis of all transcripts synthesized. These hemolysin regulatory sequences are used to promote the abundant synthesis and secretion of any adjoining downstream gene.

The vaccines of the present invention can be administered to a host, either alone or in combination with a pharmaceutically acceptable excipient, in an amount sufficient to induce an immune response to a tumor associated antigen. By "host" it is meant to include any organism capable of sustaining cancerous cells, especially a human. By "amount sufficient" it is meant a concentration of one or more recombinant L. monocytogenes, each expressing an antigen which invokes an immune response in T cells which will eradicate cells containing this antigen. The recombinant form of *Listeria monocytogenes* can express the tumor associated antigen alone or as a listeriolysin fusion protein which comprises the tumor associated antigen. Alternatively, by "amount sufficient" it is meant a concentration of one or more fusion proteins, each fusion protein comprising an antigen fused to a truncated form of listeriolysin, which invokes an immune response in T cells which will eradicate cells containing this antigen. Such amounts can be routinely determined by one of skill in the art upon this disclosure. By "pharmaceutically acceptable excipient" it is meant to include, but is not limited to, sterile distilled water, saline, phosphate buffered solutions or bicarbonate buffered solutions. The pharmaceutically acceptable excipient selected and the amount of excipient used will depend upon the mode of administration. Administration may be oral, intravenous, parenteral, intranasal, intramuscular, intravascular, intrarectal, intraperitoneal, or any one of a variety of well-known routes of administration. The route of administration may be selected in accordance with the site of different tumors. For example, for treatment of cancers of the alimentary tract, oral administration may be used. For treatment of colorectal cancer, intra-rectal immunization may be used. For the treatment of ovarian or pancreatic cancer, intraperitoneal administration may be used. However, other routes of administration may also be used. The vaccines of the present invention may be administered in the form of elixirs, capsules or suspensions for oral administration or in sterile liquids for parenteral or intravascular administration. The vaccines may be stored frozen, at 4° C., at room temperature or lyophilized.

In a preferred embodiment, the vaccines of the present invention are administered to a host either alone or in combination with another cancer therapy to inhibit or suppress the formation of tumors.

Thus, the vaccines of the present invention may be used to protect people at risk for cancer because of familial genetics or other circumstances that predispose them to certain types of cancer, e.g., cervical cancer in women whose husbands have papilloma virus. In addition, the vaccines can used as a cancer immunotherapy after debulking of tumor growth by surgery, conventional chemotherapy or radiation treatment. Following such treatments, the vaccines of the present invention can be administered so that the CTL response to the tumor antigen of the vaccine destroys remaining metastases and prolongs remission from the cancer. It is also believed that the vaccines of the present invention can be used to effect the growth of previously established tumors and to kill existing tumor cells.

The following examples are provided for illustrative purposes only and are not intended to limit the invention.

EXAMPLES

Example 1

A sequence encoding the first 420 amino acids of Listeriolysin O (LLO) and its promoter along with some upstream regulatory sequences was PCR amplified from *L. monocytogenes* chromosomal DNA (wild type strain 10403s) and ligated to PCR amplified DNA encoding NP, derived from plasmid pAPR502. (Young, J. F., U. Desselberger, P. Graves, P. Palese and A. Shatzman, "Cloning and Expression of influenza virus genes", *The Origin of Pandemic Influenza Viruses*, W. G. Laver, eds., Elsevier, New York, 1983, p. 129). The construction resulted in an in-frame fusion plus the addition of two amino acids at the site of the fusion junction. The fusion was cloned into the shuttle plasmid pAM401, a shuttle vector able to replicate in both gram+ and gram– bacteria which contains a gram+ chloramphenicol resistance gene and a gram– chloramphenicol resistance gene (Wirth, R., F. Y. An and D. B. Clewell, *J. Bacteriol.* 1986, 165, 831). The resultant plasmid, pDP1659, was introduced into wild type *L. monocytogenes* (strain 10403s) by electroporation to yield *L. monocytogenes* strain DP-L1659. This recombinant strain was clearly able to make and secrete a fusion protein of the predicted size (105 kD) as determined by western blot analysis of the secreted proteins in the culture supernatants using anti-LLO polyclonal antiserum and anti-NP monoclonal antibody. The presence of the fusion gene under the control of the LLO promoter in a multicopy plasmid resulted in reduced secretion of the chromosomally encoded LLO, but not to the extent that it prevented escape of the bacteria from the vacuole or subsequent intracytoplasmic growth. However, this strain was not stable in the absence of chloramphenicol.

To construct *L. monocytogenes* strain, DP-L2028, which is stable in vivo and which was used in Examples 2 through 6, plasmid pDP-1659 was modified by inserting the prfA gene from 10403s and then used to transform a prfA-*L. monocytogenes* mutant DP-L1075. This resulted in *L. monocytogenes* strain DPL2028 which secretes the LLO-NP fusion protein stably in vivo and in vitro.

Example 2

Treatment of Mice With LM-NP

One hundred and twenty Balb/c mice were divided into three groups of 40. One group was immunized with one-tenth of an LD50 of wild-type *L. monocytogenes*, one group was immunized with sterile saline and the third group was immunized with a recombinant *L. monocytogenes* vector transformed to secrete influenza nucleoprotein fusion protein(LM-NP). After two weeks, each group received a similar booster immunization. This immunization schedule was determined to produce strong CTL responses against influenza nucleoprotein. Two weeks after the last immunization, animals in each group were challenged subcutaneously with either CT26 or RENCA which had been transfected with the same influenza nucleoprotein gene that was used to transform the *L. monocytogenes* vector (CT26-NP or RENCA-NP, respectively) or with the parental CT26 or RENCA line. Each mouse was administered $5 \times 10^5$ tumor cells, which is 50 times the tumoricidal dose. Tumor growth was monitored every two days in these six groups of animals. Results from this study are shown in FIGS. 1 through 4. The only group showing any protection from the tumoricidal dose was the animals which received the LM-NP fusion protein and which were challenged with the relevant tumor cell expressing NP. In the CT26-NP group, after 25 days, 6 of the animals showed no detectable tumor growth, 3 had tumors of less than 5.0 mm and one had a tumor of 9.0 mm. In the RENCA-NP group, none of the animals showed any signs of tumor growth. In contrast, all the mice in the other groups have tumors between 1.5 and 3.0 cm.

In order to maintain the foreign NP gene, CT26-NP is usually maintained on the antibiotic G418. It is believed that the small number of CT26-NP tumor cells that grew in the LM-NP immunized mice are cells which have lost the NP gene in the absence of G418.

Example 3

Figure 5A:
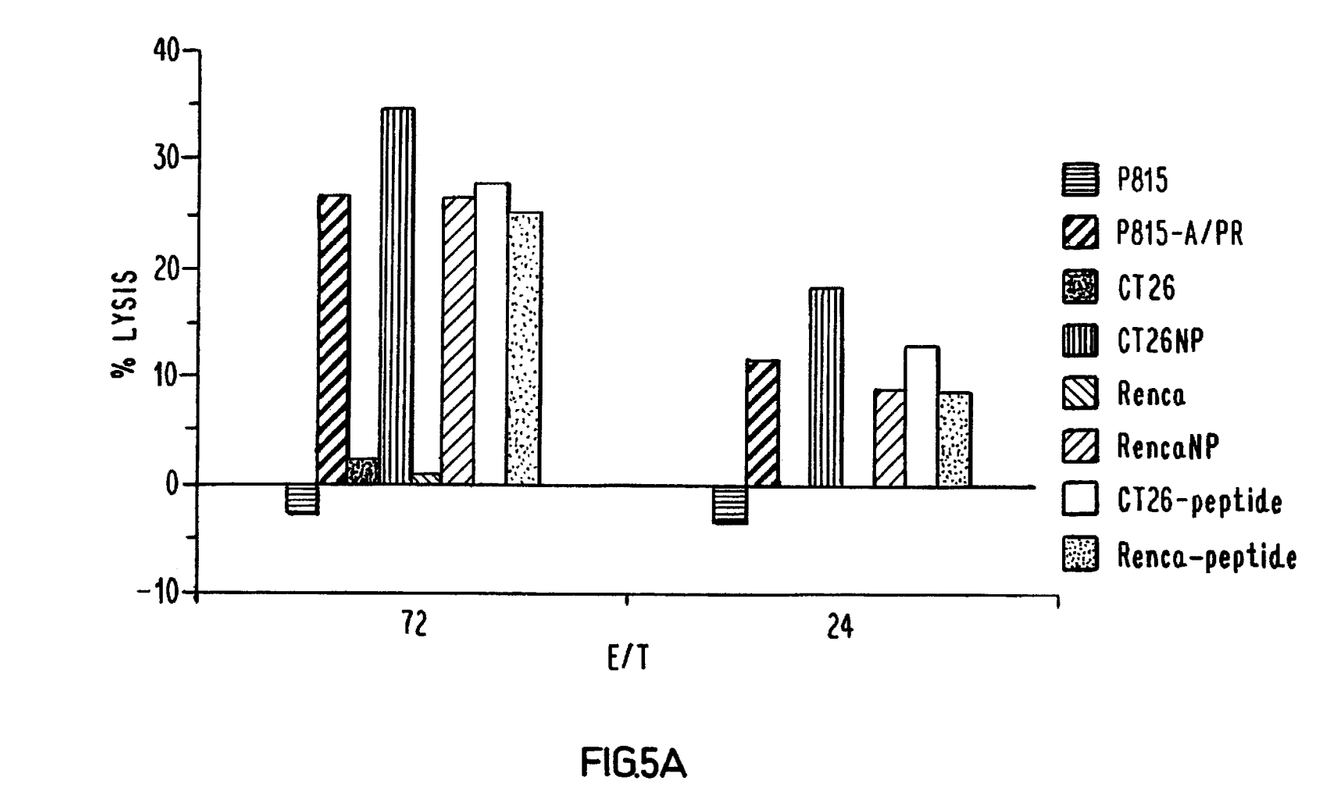
FIG. 5A shows effectors stimulated with A/PR/8.
Figure 5B:
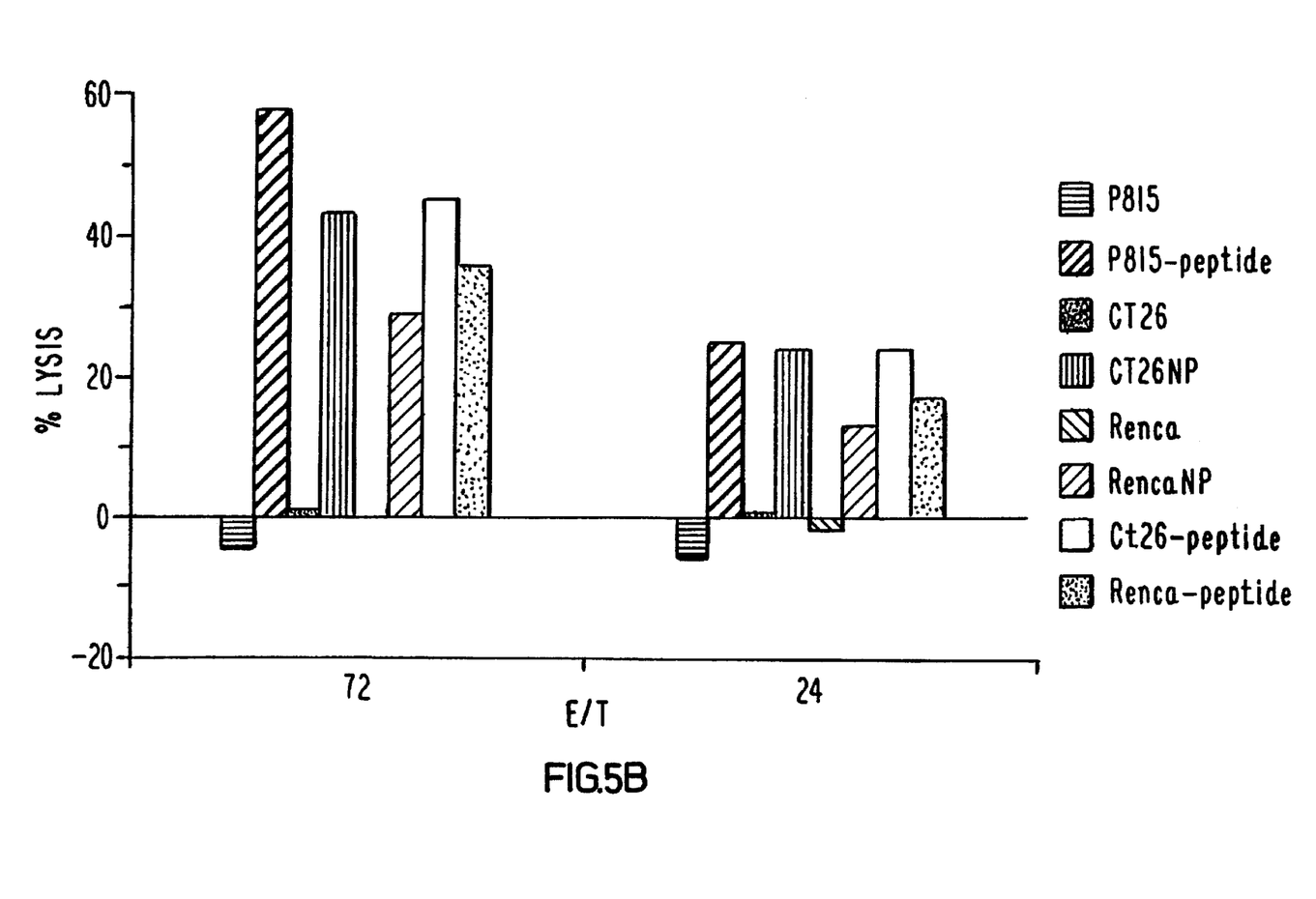
FIG. 5B shows effectors stimulated with peptides.

CTL Generated by Immunizing Balb/c Mice With LM-NP can kill tumor cells CT26 and RENCA that express NP In Vitro Mice were immunized with 0.1 LD$_{50}$ of LM-NP. Two weeks later, the mice were sacrificed and primary cultures were set up of spleen cells with either influenza infected (A/PR8/34) splenocytes (FIG. 5A) or with a synthetic peptide 147–158 known to represent the immunodominant epitope of the NP protein (FIG. 5B). After four days in culture, the cytolytic activity of both populations was measured against CT26-NP, RENCA-NP and the parental cell lines CT26 and RENCA. A positive control was included (P815, a mastocytoma tumor cell line known to be efficiently lysed by H-2$^d$ restricted CTL in the presence of the peptide or when infected by A/PR8/34). As FIG. 5A shows, RENCA-NP and CT26-NP, but not the parental lines, were lysed by NP specific effectors induced by immunizing with LM-NP and expanded with A/PR8/34. In FIG. 5B, a similar experiment in which the effectors were expanded with peptide show similar results.

Example 4

Immunization by LM-NP Will Cause Elimination of RENCA Tumor Growth

In this experiment, immunization with LM-NP after tumor growth had been initiated caused regression and depletion of tumors. Tumor cells ($5 \times 10^5$) were introduced subcutaneously to 30 mice. On Day 13, after measurable tumors (5 mm) had grown in the mice, they were divided into three groups of ten. Ten mice received LM-NP, 10 mice received wild type *Listeria monocytogenes* and ten received no further treatment. On Day 23 the mice were immunized again with either LM-NP or wild type *Listeria monocytogenes*. As FIG. 6 shows, only the mice that received the LM-NP fusion protein show regression of tumor growth to the point where the tumor was no longer visible in 9 out of 10 mice.

Example 5

Immunization by LM-NP Will Cause Cessation of CT26NP Tumor Growth

The experiment described in Example 4 was also done with the colorectal CT26-NP tumor cells. CT26-NP is a much faster growing tumor and is also more unstable in its expression of NP. Nevertheless, in this experiment, it was also found that immunization by LM-NP after tumor growth has been initiated halts tumor growth. Tumor cells ($5 \times 10^5$) were introduced subcutaneously to 30 mice. On day 10, after measurable tumors (5 mm) had grown in the mice, they were divided into three groups of ten. Ten mice received LM-NP, 10 mice received wild type *Listeria monocytogenes*, and 10 mice received no further treatment. On day 17 the mice were immunized again with either LM-NP or wild type *Listeria monocytogenes*. As FIG. 7 shows, only the mice that received the LM-NP fusion protein show a change in tumor growth. However, unlike the case with RENCA, regression of growth was not observed in as many mice. This may be because by Day 17, instability of the CT26-NP tumor cells resulted in many of the tumor cells losing the NP antigen.

Example 6

Inhibition of Tumor Growth is Caused by CD8+ T Cells

Figure 8:
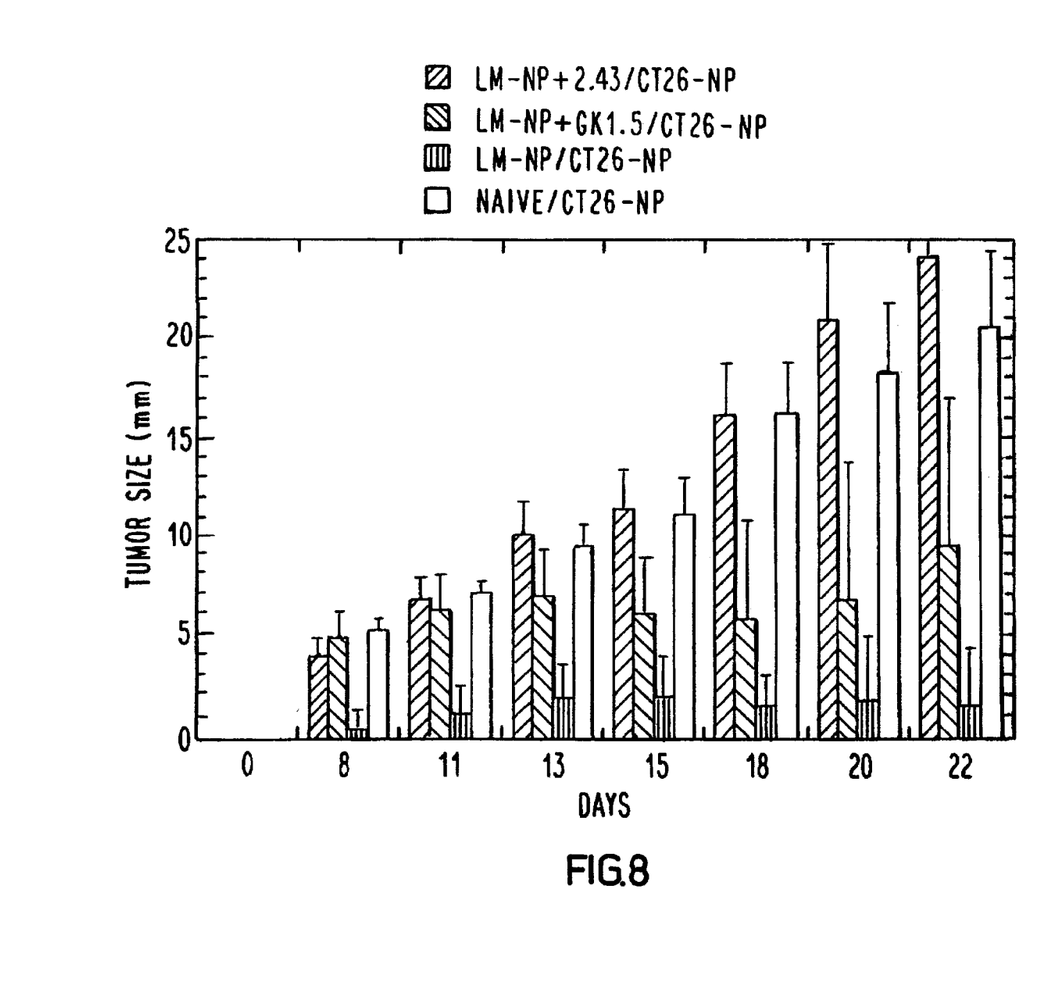
FIG. 8 is a bar graph which provides data from experiments wherein it was shown that inhibition of tumor growth is caused by CD8+ T cells.

In this experiment, 30 mice were immunized with LM-NP using the same protocol as discussed in Example 2. Ten days after the last immunization, 10 mice were depleted of CD8+ cells by immunizing with antibody 2.43 (specific for the CD8 molecule); 10 mice were depleted of CD4+ cells by immunizing with GK 1.5 (specific for the CD4 molecule); and 10 mice were left with a complete T cell repertoire. (The protocol for depletion of CD8+ or CD4+ T cells was that as described by A. Kruisbeek, *Current Protocols In Immunology*, Coligan et al., eds, John Wiley & Sons, Inc., 1994, V.1, 4.1.1–4.1.2). After T cell depletion, the mice were challenged subcutaneously with $5 \times 10^5$ CT26-NP cells per mouse. As a control, 10 naive mice were also challenged with the same dose. As FIG. 8 shows, the group of mice in which the CD8+ T cell subset was depleted showed similar tumor growth to the control (naive) group of mice. The mice in which the CD4+ T cell subset was depleted showed reduced protection against tumor growth, indicating that CD4+ cells play an accessory response in the control of tumor growth; and the mice with a complete T cell repertoire show protection against tumor growth induced by the LM-NP fusion protein.

What is claimed is:

1. A method of inducing an immune response to a protein expressed by tumor cells in a host comprising administering to a host an effective amount of a vaccine comprising a fusion protein of a protein expressed by tumor cells fused to a truncated form of listeriolysin, or a recombinant form of *Listeria monocytogenes* which grows and spreads and expresses said protein expressed by tumor cells so that an immune response to said protein expressed by tumor cells, which is measured by inhibition of growth of the tumor cells expressing said protein, is induced.

2. The method of claim 1 wherein said vaccine comprises a recombinant form of *Listeria monocytogenes* that expresses a listeriolysin fusion protein comprising said protein expressed by tutor cells.

* * * * *